US011957869B2

(12) United States Patent
Dave et al.

(10) Patent No.: US 11,957,869 B2
(45) Date of Patent: Apr. 16, 2024

(54) DUAL MODE GEOFENCING FOR MEDICAL DEVICES

(71) Applicant: CareFusion 303, Inc., San Diego, CA (US)

(72) Inventors: Jay Dave, San Diego, CA (US); Igor Nesterenko, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 501 days.

(21) Appl. No.: 17/010,588

(22) Filed: Sep. 2, 2020

(65) Prior Publication Data

US 2021/0077712 A1 Mar. 18, 2021

Related U.S. Application Data

(60) Provisional application No. 62/900,368, filed on Sep. 13, 2019.

(51) Int. Cl.
*A61M 5/142* (2006.01)

(52) U.S. Cl.
CPC .......... *A61M 5/14244* (2013.01); *A61M 2005/14208* (2013.01); *A61M 2205/18* (2013.01);
(Continued)

(58) Field of Classification Search
CPC .... A61M 2005/14208; A61M 2205/18; A61M 2205/3553; A61M 2205/502; A61M 2205/8206; A61M 5/14244
See application file for complete search history.

(56) References Cited

U.S. PATENT DOCUMENTS

| | | |
|---|---|---|
| 5,713,856 A | 2/1998 | Eggers et al. |
| 7,163,381 B1 | 1/2007 | Barak |

(Continued)

FOREIGN PATENT DOCUMENTS

| | | |
|---|---|---|
| EP | 2404253 A1 | 1/2012 |
| EP | 2947543 A1 | 11/2015 |

(Continued)

OTHER PUBLICATIONS

International Search Report and Written Opinion for Application No. PCT/US2020/049270, dated Dec. 1, 2020, 19 pages.

(Continued)

*Primary Examiner* — Quynh-Nhu H. Vu
(74) *Attorney, Agent, or Firm* — Morgan, Lewis & Bockius LLP

(57) ABSTRACT

An infusion pump includes a housing, a wireless transceiver, a pump motor mounted within the housing, a location sensor configured to provide information associated with a location of the infusion pump, a battery conductively coupled to the wireless transceiver, the pump motor, the location sensor and processor(s), and memory. The infusion pump is configured to monitor, using the location sensor, a geofence parameter of the infusion pump, determine a change in the location of the infusion pump based on the geofence parameter, identify an operation mode of the infusion pump associated with the geofence parameter, and automatically switch, responsive to the changed location, the operation mode of the infusion pump from a first mode currently programmed for care of a patient to a second mode, the second mode using different parameters than the first mode to control elements of the infusion pump.

17 Claims, 5 Drawing Sheets

(52) U.S. Cl.
CPC ............... *A61M 2205/3553* (2013.01); *A61M 2205/502* (2013.01); *A61M 2205/8206* (2013.01)

(56) References Cited

U.S. PATENT DOCUMENTS

| | | | |
|---|---|---|---|
| 8,936,565 B2 | 1/2015 | Chawla | |
| 9,078,971 B2 * | 7/2015 | Scarpaci | A61M 1/1522 |
| 9,335,910 B2 * | 5/2016 | Farnan | A61M 5/14244 |
| 2008/0300572 A1 * | 12/2008 | Rankers | A61B 5/14532 |
| | | | 604/504 |
| 2012/0232520 A1 | 9/2012 | Sloan et al. | |
| 2013/0184638 A1 | 7/2013 | Scarpaci et al. | |
| 2013/0245387 A1 | 9/2013 | Patel | |
| 2016/0051749 A1 * | 2/2016 | Istoc | A61M 5/1723 |
| | | | 604/67 |
| 2019/0046035 A1 * | 2/2019 | Nyquist | A61B 5/0205 |

FOREIGN PATENT DOCUMENTS

| | | |
|---|---|---|
| WO | WO-2018013842 A1 | 1/2018 |
| WO | WO-2019032435 A1 | 2/2019 |

OTHER PUBLICATIONS

BD, "BD Alaris™ Guardrails™ Suite MX", Becton, Dickinson and Company, date unknown, Copyright 2023, retrieved from: https://www.bd.com/en-us/offerings/capabilities/infusion-therapy/infusion-system-software/guardrails-suite-mx-software.

TIBCO, "TIBCO Announces Acquisition of Master Data Management Leader Orchestra Networks" TIBCO Software Inc., Dec. 4, 2018, Copyright 2023 Cloud Software Group, Inc., retrieved from: https://www.tibco.com/press-releases/2018/tibco-announces-acquisition-master-data-management-leader-orchestra-networks.

Chinese Office Action for Application No. 202080064457.2, dated Dec. 28, 2023, 29 pages including translation.

* cited by examiner

DUAL MODE GEOFENCING FOR MEDICAL DEVICES

CROSS-REFERENCES TO RELATED APPLICATIONS

This Application claims the benefit of U.S. Provisional Patent Application No. 62/900,368 entitled "DUAL MODE GEOFENCING FOR MEDICAL DEVICES," filed on Sep. 13, 2019, the disclosure of which is hereby incorporated by reference in its entirety for all purposes.

TECHNICAL FIELD

This application relates generally to adjusting operational features of a medical device based on where the medical device is located.

BACKGROUND

A medical device may be used in a hospital or clinical setting and then moved for use in another location, such as a patient's home. Protocols, user interfaces, monitoring parameters, and other operational functions of the medical device used in the clinical setting where the medical device operator is a trained healthcare provider (e.g., doctor, nurse, medical technician) may be inappropriate in the home setting where the medical device operator is the patient or a family member. Improper use of the medical device in the home setting increases the health risk to the patient.

SUMMARY

According to various aspects, the subject technology provides a medical device configured to monitor, using one or more sensors, a geofence parameter of a medical device, and to determine when a location setting of the medical device changes. Responsive to a change in the location setting, an operation mode of the medical device is automatically switched from a first mode currently programmed for the care of the patient to a second mode, the second mode using different parameters than the first mode to control the medical device.

One or more embodiments of the disclosure provide for an infusion pump. The infusion pump includes a housing, a wireless transceiver, a pump motor mounted within the housing, a location sensor configured to provide information associated with a location of the infusion pump, a battery conductively coupled to the wireless transceiver, the pump motor, and the location sensor. The pump motor is mounted within the housing and a force from the pump motor causes delivery of a fluid from a fluid source to a patient. The batter provides power to activate the pump motor and the location sensor and to communicate messages via the wireless transceiver. The infusion pump also includes one or more processors conductively coupled with the battery and memory. The infusion pump is configured to monitor, using the location sensor, a geofence parameter of the infusion pump, determine a change in the location of the infusion pump based on the geofence parameter, identify an operation mode of the infusion pump associated with the geofence parameter, and automatically switch, responsive to the changed location, the operation mode of the infusion pump from a first mode currently programmed for care of a patient to a second mode, the second mode using different parameters than the first mode to control at least one of the batter, the pump motor, or the wireless transceiver of the infusion pump.

One or more embodiments of the disclosure provide for a method. The method includes monitoring, using one or more sensors, a geofence parameter of a medical device. The method also includes determining a change in a location setting of the medical device based on the geofence parameter. The method further includes automatically switching, responsive to the changed location setting, an operation mode of the medical device from a first mode currently programmed for care of a patient to a second mode, the second mode using different parameters than the first mode to control the medical device.

In one or more aspects, switching the operation mode of the medical device includes switching from a clinician based functional module to a non-clinician based functional module. In one or more aspects, switching the operation mode of the medical device includes switching from a non-clinician based functional module to a clinician based functional module. In one or more aspects, the medical device includes an infusion device and the one or more sensors includes one of a global positioning system receiver, a radio frequency receiver, a Bluetooth receiver and a cellular receiver, and the operation mode is associated with a pumping mechanism administering a fluid to the patient. In one or more aspects, the method further includes determining a battery capacity of a battery powering the medical device; determining, based on the location setting exceeding a distance range, that the battery capacity is insufficient to power the medical device for a predetermined period of time; and generating an alert according to an alerting sequence associated with the second mode.

In one or more aspects, the second mode is associated with a clinical care facility and the alerting sequence matches alerting escalation rules of the clinical care facility. In one or more aspects, the second mode is associated with a home care location and the alerting sequence matches home alerting escalation rules. In one or more aspects, the method further includes determining a quantity of medication available to be dispensed by the medical device; determining, based on the location setting exceeding a distance range, that the quantity of medication is insufficient to follow a current medication dispensing protocol of the medical device; and generating an alert according to an alerting sequence associated with the second mode. In one or more aspects, switching the operation mode of the medical device includes switching information provided on a user interface device. In one or more aspects, the information provided on the user interface device is one of a clinician interface configured for use by a trained clinician and a simplified format interface configured for use by a non-clinical user.

One or more embodiments of the disclosure provide for a medical device. The medical device includes one or more processors and memory including instructions. The instructions, when executed by the one or more processors, cause the medical device to monitor, using one or more sensors, a geofence parameter of a medical device; determine a change in a location setting of the medical device based on the geofence parameter; and automatically switching, responsive to the changed location setting, an operation mode of the medical device from a first mode currently programmed for care of a patient to a second mode, the second mode using different parameters than the first mode to control the medical device.

In one or more aspects, switching the operation mode of the medical device includes one of switching from a clinician based functional module to a non-clinician based functional module and switching from a non-clinician based functional module to a clinician based functional module. In one or more aspects, the medical device includes an infusion device and the one or more sensors comprises one of a global positioning system receiver, a radio frequency receiver, a Bluetooth receiver and a cellular receiver, and the operation mode is associated with a pumping mechanism administering a fluid to the patient. In one or more aspects, the instructions, when executed by the one or more processors, further cause the medical device to: determine a battery capacity of a battery powering the medical device; determine, based on the location setting exceeding a distance range, that the battery capacity is insufficient to power the medical device for a predetermined period of time; and generate an alert according to an alerting sequence associated with the second mode. In one or more aspects, one of the second mode is associated with a clinical care facility and the alerting sequence matches alerting escalation rules of the clinical care facility, and the second mode is associated with a home care location and the alerting sequence matches home alerting escalation rules.

In one or more aspects, the instructions, when executed by the one or more processors, further cause the medical device to: determine a quantity of medication available to be dispensed by the medical device; determine, based on the location setting exceeding a distance range, that the quantity of medication is insufficient to follow a current medication dispensing protocol of the medical device; and generate an alert according to an alerting sequence associated with the second mode. In one or more aspects, switching the operation mode of the medical device includes switching a user interface module. In one or more aspects, the user interface module is a clinician user interface configured for use by a trained clinician. In one or more aspects, the user interface module is a patient user interface configured for use by one of a patient and a non-trained user associated with the patient.

One or more embodiments of the disclosure provide for a non-transitory machine-readable storage medium embodying instructions that, when executed by a machine, cause the machine to perform operations. The operations include, monitoring, using one or more sensors, a geofence parameter of a medical device; determining a change in a location setting of the medical device based on the geofence parameter; and automatically switching, responsive to the changed location setting, an operation mode of the medical device from a first mode currently programmed for care of a patient to a second mode, the second mode using different parameters than the first mode to control the medical device.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

The subject technology includes a system that utilizes sensors and/or other operational features of a medical device (e.g., such as an infusion pump) to collect signals and to, based on those signals, detect the location of the device and/or the environment in which the device is operated. According to some implementations, the medical device may adjust operational features based on the location or environment of the medical device.

For example, in some care areas, such as monitored care facilities (e.g., hospital, clinic), the setup, operation, alerting and routine maintenance of the medical device is handled by a trained healthcare provider. In this regard, a comprehensive user interface and an alerting escalation process matching the care facility rules may be provided. However, in a home care area, the operation of the medical device is likely done by the patient and/or family members who are not trained healthcare workers. In this regard, a streamlined and less complex user interface may be provided, as well as an alerting escalation process directed to home rules. According to various aspects of the subject technology, a medical device is configured to, when there is a change in the location and/or environment of the medical device, adjust or change operational modes to rely on the appropriate care facility or home functions and processes.

Figure 1:
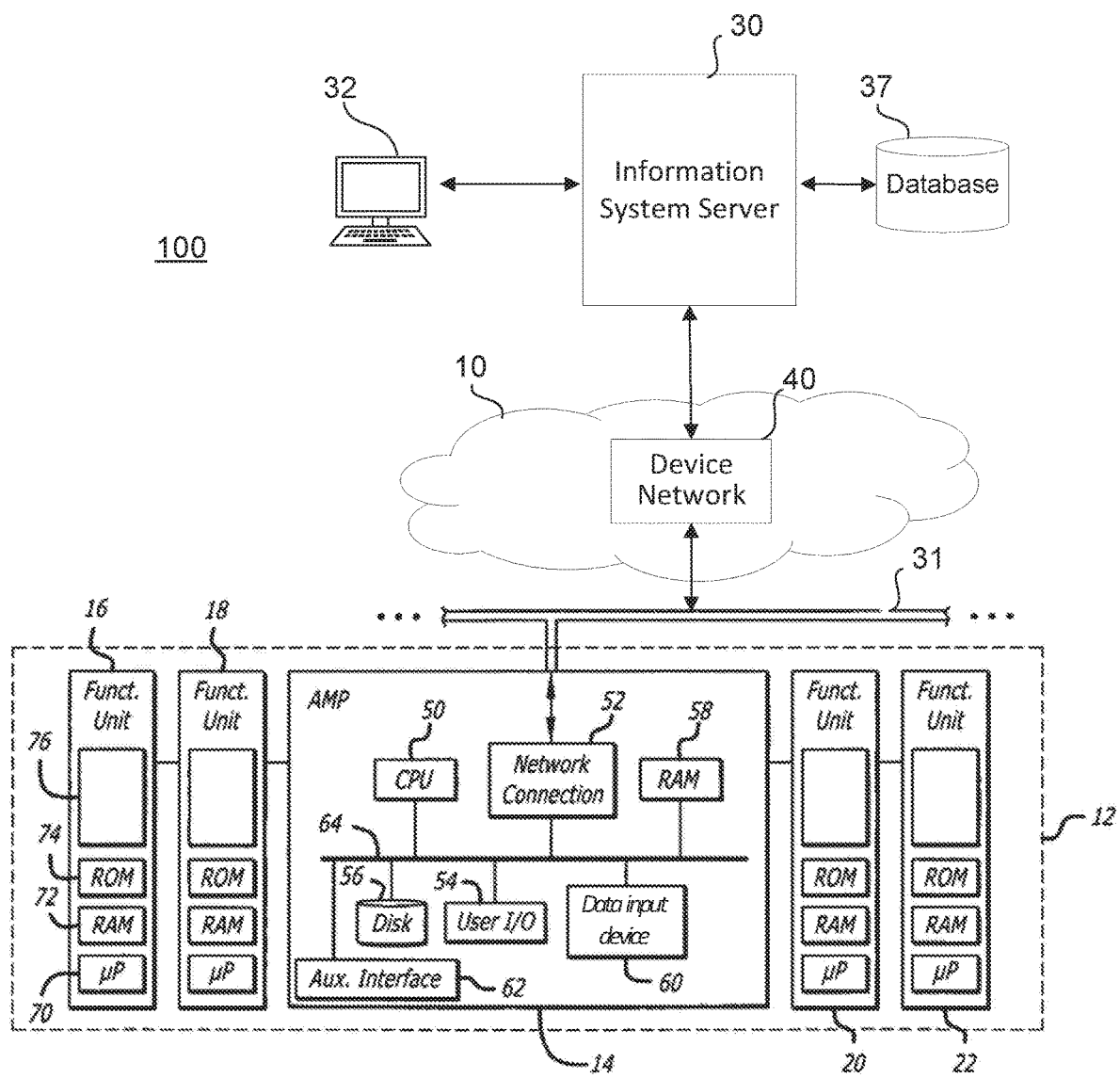
FIG. 1 depicts an example of an institutional patient care system of a healthcare organization, according to aspects of the subject technology.

FIG. 1 depicts an example of an institutional patient care system 100 of a healthcare organization, according to aspects of the subject technology. In FIG. 1, a patient care device (or "medical device" generally) 12 is connected to a healthcare facility network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each medical device 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a healthcare facility. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which patient care devices 12 (and other devices) communicate in accordance with normal operations.

Additionally, institutional patient care system 100 may incorporate a separate information system server 30, the function of which will be described in more detail below. Moreover, although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, and mobile devices such as laptops, tablet computers, augmented reality devices, or smartphones, configured with software for communications with information system server 30 via network 10.

Patient care device 12 comprises a system for providing patient care, such as that described in U.S. Pat. No. 5,713,856 to Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module or unit 14, also referred to as interface unit 14, connected to one or more functional modules 16, 18, 20, 22. The functional elements of the patient care device 12 may be included within or mounted upon a single housing or modular housing elements including connective structures to attach and detach the modules from other modules included in the patient care device 12. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device.

Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with control unit 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1, any number of devices may be connected directly or indirectly to central control unit 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. The configuration database may be a database on storage unit 56 internal to patient care device 12, or an external database 37. A particular configuration database is selected based, at least in part, by patient-specific information such as device or patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through network connection 52 or any of input/interface devices 54, 60 or 62, and may originate from anywhere in network 10, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

A medical device including one or more of the features described may be implemented an ambulatory medical device. Ambulatory medical devices generally refer to devices designed to be portable to support administration of medication during transportation of a patient or remote medication administration (e.g., outside of a health care facility such as in a user's home). U.S. Pat. No. 7,163,381 to Barak describes a pump that may be suitable for ambulatory care and modified to include the geofencing features described to assist in providing safe administration during mobility events. The disclosure of U.S. Pat. No. 7,163,381 is incorporated by reference in its entirety.

Figure 2:
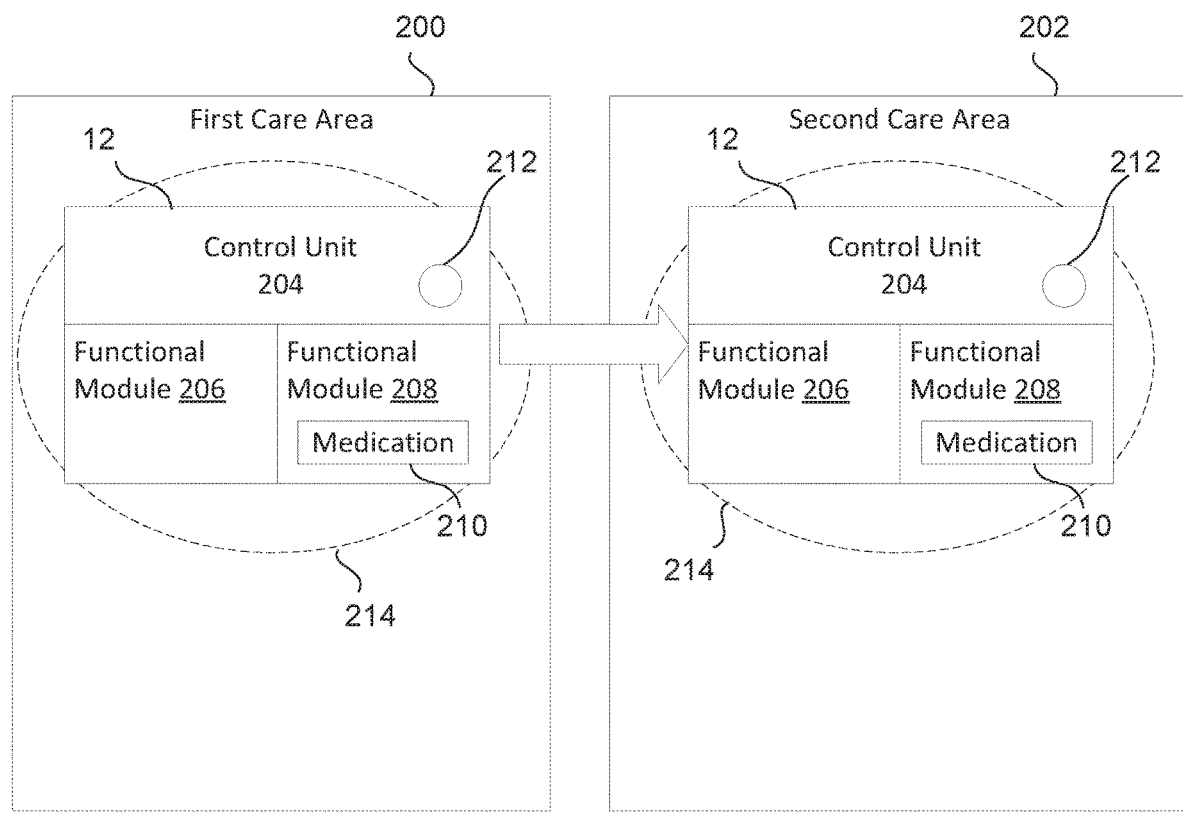
FIG. 2 depicts an example of a medical device moving between patient care areas, and detecting a location condition, in accordance with aspects of the subject technology.

FIG. 2 depicts an example of a medical device 12 moving between a first care area 200 and a second care area 202 (e.g., healthcare facility to a patient's home), and detecting the change in location and/or environment, in accordance with aspects of the subject technology. As shown, a medical device 12 may include a control unit 204 and one or more functional modules (e.g., functional modules 16, 18, 20, 22), including a first functional module 206 and a second functional module 208. The second functional module 208 is depicted as including a medication 210. In some implementations, medical device 12 may be a dispensing device configured to, on authorizing by a clinician, dispense the medication 210 for care of the patient. In some implementations, medical device 12 may be an infusion device configured to administer the medication 210 to the patient (e.g., intravenously by way of a connected infusion set). Control unit may include one or more processors such as to be configured to interface with the functional units and to control and provide power to the functional units when the functional units are connected to the control unit.

According to various aspects of the subject technology, medical device 12 may include one or more sensors 212 configured to detect location and/or environments. Medical device 12 may be configured to monitor, using sensor(s) 212, geofencing parameters of the medical device 12. In this regard, sensor(s) 212 may include a global positioning system (GPS) receiver, a radio frequency (RF) receiver, a Bluetooth receiver, a cellular (LTE) receiver, and the like. For example, a sensor 212 may be configured to detect the physical location of the medical device 12, as well as to interact with a communication network (e.g., healthcare facility network, home wireless network). Sensor(s) 212 may have a range 214.

Medical device 12 may include circuitry that causes sensor(s) 212 to obtain a measurement value representative of the environmental condition. Sensor(s) 212 may measure the environmental condition periodically, or upon certain trigger conditions. One example trigger condition may include the medical device 12 detecting that it has moved to a new location (e.g., from a clinical setting to a patient's home). Medical device 12 may query an internal database on storage unit 56 or a server 30 and/or a corresponding external database 37 based on its known coordinates (e.g., GPS) or based on connecting to a new WiFi system to determine whether its new physical environment is a monitored care facility (e.g., hospital, clinic) or is a remote patient location (e.g., home, hotel, vehicle).

According to various implementations, the medical device 12 may be provisioned with geofencing information, where the geofence may identify monitored care facilities and all other locations are considered "home." In some implementations, the geofencing information may identify a "home" area, such as the patient's main residence. Geofencing information for the medical device 12 may be specified by the care facility (e.g. hospital) and can also be refined by a patient (e.g. multiple homes). When detected within a geofenced area considered to be a care facility, the medical device 12 may adjust the alerting escalation to behave according to the care facility rules. When detected outside the geofenced area, the medical device 12 may adjust the alerting escalation to behave according to "home" rules. For example, the first care area 200 may be a hospital, in which the medical device 12 operates according to hospital escalation rules, and the second care area 202 may be a patient's primary home residence, in which the medical device 12 operates according to different residential escalation rules.

According to various implementations, home rules may include a specific order or sequence of contacts (e.g., child, spouse, doctor, home healthcare provider). Home rules may include a mode of contact (e.g., text, voice call). Home rules may use location to further identify the proper sequence of contacts. For example, a patient may split time between two locations (e.g., elderly patient with children). Thus, when the identified geofencing location of medical device 12 is near child 1, child 1 may be listed at the top of the alerting sequence to be used by the medical device 12. Similarly, when the identified geofencing location of medical device 12 is near child 2, child 2 may be moved to the top of the alerting sequence to be used by the medical device 12.

According to various implementations, alerting may be based on the location of the patient (e.g., away from a geofenced area). For example, the location of the patient while operating the medical device 12 in "home" mode may be detected and used to assess proper functioning of the medical device 12. In one example, the battery life of the medical device 12 may be sensed. Here, if the distance of the medical device 12 from the first care area 200 (e.g., medical care facility) or the second care area 202 (e.g., patient's home) indicates that the medical device 12 will exceed the battery life available, an alert may be provided to ensure that the patient does not get stranded without sufficient battery life for the medical device 12. Another example of location based alerting is the volume remaining of the medication or a medication container (e.g., IV bag) associated with the medical device 12. Based on the initial programming of the medical device 12, the total medication to be dispensed is known (e.g., for an infusion pump, the total amount of medication to be infused should be known along with a rate of infusion). Here, if the patient moves away from a geofenced area (e.g., home or a care facility) at a distance that would cause the current medication supply to be exhausted, an alert may be provided so the patient does not get stranded without sufficient medication.

According to various implementations, the information and feedback presented by the user interface 54 to the user may be based on the location of the medical device 12, such as a medical care facility or a patient's home. For example, because the home user (e.g., patient, patient's family member or friend) may not be as highly trained as a clinician, the interface and feedback may be adjusted based on the location of the medical device 12. Here, if the medical device 12 is determined to be in the patient's home, the user interface device 54 may provide more feedback to the user (e.g. context-based help) than a trained clinician requires, or the information on the user interface device 54 may be presented in simplified format (e.g., larger font, contrasting colors) to reduce complexity and errors in controlling the medical device 12. For example, the medical device 12 may have a clinical interface module for use in clinical settings that provides information in standard clinician terms and/or with minimal labeling or prompting. By contrast, the medical device 12 may have a patient interface module for use in non-clinical settings that provides information in laymen's terms, with an increased use of visual aids and explanatory text. The medical device 12 may be configured to automatically switch between the clinical interface and patient interface modules based on determining the geofenced location of the medical device 12.

According to various implementations, compliance monitoring may be heightened if the geofenced location of the medical device 12 is determined to be a non-clinical setting. For example, medical device 12 may be configured to improve patient compliance with a prescribed regimen by activating a different monitoring mode when detected outside the care facility (e.g., in "home" area). In the example of medical device 12 being an infusion pump, compliance may include timing of infusions, infusion parameters (e.g., rate, volume, type of drug), etc. Thus, if a scheduled infusion time arrives when the pump is in home mode and the infusion has not started, the pump may transmit an alert or reminder to indicate the scheduled treatment.

According to various implementations, compliance may include inventory control features. For example, a patient may have a stock of medication for dispensing (e.g., infusing), where different doses of medication may have different expiration dates. This may lead to the patent using one dose that has an expiration date after the expiration date of another dose. To minimize or avoid spoilage or using expired doses, the patient care system 100 or the medical device 12 may check the patient's inventory of medication and provide an alert if the patient attempts to deviate from a first in/first out (FIFO) dose usage. By contrast, the pharmacy dispensing processes at clinical facilities and/or clinician training in dispensing medications by a FIFO process may obviate the need or desire for such home based alerting.

According to various implementations, specific controls may be implemented for a non-clinical setting dispensing of controlled medications (e.g., opioids). For example, a home based user may be using the medical device 12 for dispensing controlled medications. In such instances, it may be desirable to adjust medical device 12 functions to prevent abuse and/or overuse of the controlled medications. For example, an infusion pump may be configured to deliver a specified amount of an opioid drug during a set time, and blocking or preventing infusion of an additional amount of the opioid drug or any other additional drug that may interact with the opioid drug. The medical device 12 may also restrict programming options to prevent programming for abusive use (e.g., bolas opioid) in a home setting.

When receiving a geofence value, medical device 12 may determine when the value dictates operation of the medical device 12 with regard to care of a patient in a clinical mode or a home mode. Responsive to the value determination, an operation mode of the medical device 12 may be automatically switched from a first mode currently programmed for the care of the patient to a second mode (e.g., clinical mode to home mode). According to various aspects, the second mode may utilize different parameters than the first mode to control the medical device. For example, a first mode may operate a pump according to a first flow rate, and a second mode may operate the pump according to a second, lower flow rate. A parameter of a first mode may activate a functional module, and parameter of a second mode may deactivate the functional module. Also, a parameter of the first mode may provide a clinical setting alert and/or user interface process, while a parameter of the second mode may provide a non-clinical or home setting alert and/or user interface process.

Computer program code for carrying out operations of the subject technology may be written in an object oriented programming language such as, for example, JAVA®, Smalltalk, or C++. However, the computer program code for carrying out operations of the subject technology may also be written in conventional procedural programming languages, such as the "C" programming language, in an interpreted scripting language, such as Perl, or in a functional (or fourth generation) programming language such as Lisp, SML, Forth, or the like. The software may also be written to be compatible with HLA-7 requirements.

According to various implementations, the medical device 12 may include and/or utilize one or more location sensors that are configured to measure location parameters and assign values representative of the location setting. The medical device 12 may include circuitry and/or software that monitors the measurements and/or values received from each of these sensors. When a medical device 12 (or its network circuitry) detects that one of these measurements and/or values satisfies (e.g., exceeds) a predetermined geofence threshold, the medical device may be triggered to automatically adjust or change modes to align with the determined geofenced location.

According to various implementations, adjusting or changing a mode of operation may include taking a corrective action. A corrective action may include displaying an alert on the medical device and/or sounding an audible alert. A corrective action may include stopping an ongoing administration of a medication or locking the device from administering or providing further medications until the alert has been acknowledged. In a clinical setting, acknowledgement may include identifying a clinician authorized to the medical device by way of the clinician scanning a badge, and the clinician manually dismissing the alert by way of a manual input at the medical device or by way of a computing device connected to the medical device (e.g., over a network). In a home setting, acknowledgement may include providing patient oriented step by step instructions to the home user (e.g., patient, home caregiver), and the home user manually dismissing the alert by way of a manual input at the medical device or by way of a computing device connected to the medical device (e.g., over a network).

Many medical devices may be battery operated, so that the devices may maintain operations in the event of a power outage or when moving between care areas. The battery unit of a medical device may provide power to, for example, one or more processors responsible for operations, a pumping mechanism (e.g., in the case of an infusion pump), an electronic lock (e.g., in the case of a dispensing device), or network circuitry. The battery unit may also be responsible for providing power to subordinate or secondary devices connected to the medical device. For example, a battery unit of an infusion device may provide power to one or more connected functional modules that each include an infusion pump, a syringe pump, a PCA pump, an epidural pump, an enteral pump, a blood pressure monitor, a pulse oximeter, an EKG monitor, an EEG monitor, a heart rate monitor, an intracranial pressure monitor, or the like.

In some implementations, the medical device 12 may utilize one or more geofence sensors to detect a location setting in which the device is located. One or more location measurements may be obtained using the geofence sensor(s) and used to determine whether to adjust a power allotment to the various systems of the medical device 12, including to any connected functional modules. Certain parameters may tend to shorten a battery's capacity and life, such as environmental parameters (e.g., controlled temperature of a clinical setting versus ambient temperature on a patio outside a patient's home) and/or the availability of charging outlets. A medical device may obtain data regarding its battery's expected capacity or life based on various factors including current operating temperature, depth of discharge, rate of discharge, and previously known capacities under similar conditions. If the medical device 12 determines that the battery's expected capacity is lower than a predetermined threshold for maintaining current operations for a predetermined time period, the medical device may enter a power saving mode and begin to shut down or reduce operation of non-essential systems. Functional units and or medical device features may be determined to be essential or non-essential depending on various factors, including care area, status of the patient, time to next charge, etc. In some examples, network connectivity may be identified as a non-essential system. In other examples, network connectivity may be identified as an essential system. Audible alarms may be identified as essential in high traffic noisy critical care areas such as an intensive care unit, but not when the device is identified as being in transit from one area to another (e.g., vehicle ride from hospital to home).

In one example, a control unit associated with an infusion pump configured according to the subject technology may monitor the device location and determine that a battery does not have enough capacity to operate the pumping mechanism(s) at a currently set flow rate for a period of time required for medicating the patient prior to receiving a next charge. The predetermined period of time may be a default period of time for operating during a power loss, may be set by the user via a configuration menu on the device, or may be provided to the infusion pump (or other medical device) by the hospital information server in connection with instructions for relocating the device from a first care unit to a second care unit. In response to determining that the battery does not have the capacity to maintain the current pumping load, the control unit may automatically enter a power saving mode and reduce the pumping rate to a level such that that the pumping mechanism may continue pumping throughout the required period of time. In some implementations, the control unit may shut down non-essential functioning units (such as a blood pressure device or pulse oximeter) while maintaining operation of essential functional units such as the pumping mechanism responsible for pumping a life-supporting medication. The control unit may also lock out the potential for module connectivity such that additional functional modules may not be attached while the device is in the power saving mode.

Some environmental conditions may cause a medical device to lose network connectivity. For example, some clinical care areas may include shielded rooms (such as MM rooms) that prevent radio and electromagnetic energy from passing through walls and some home setting areas may include sparsely populated areas with little or no wireless reception (e.g., vacation home in the mountains). When a medical device (or its network circuitry) detects it has lost network connectivity, the medical device may be triggered to automatically adjust or change modes. In one example, on detecting a loss of network connectivity, a medical device may switch to a manual mode in which it begins using an onboard drug library instead of looking up operating parameters and limits via the network connection.

In some implementations, a medical device may be configured to produce audible or visual alerts prior to or when changing modes. In this regard, the medical device, on losing a network connection, may provide on its associated display device an option for mode adjustment. For example, the medical device may prompt a user to select whether to maintain the current mode or adjust the network setting. Options may include selecting from available networks, or selecting a different type of network to use (e.g., Bluetooth or wired instead of WiFi). In some implementations, alerts may be escalated as environmental conditions worsen. For example, as more critical life-supporting systems are impacted different levels of alerts may be produced. A first alert may include a visual alert, while an audible alert may progressively come louder according to different thresholds of impact, with higher impacts leading to network messages being sent to a primary caregiver via the network.

Figure 3:
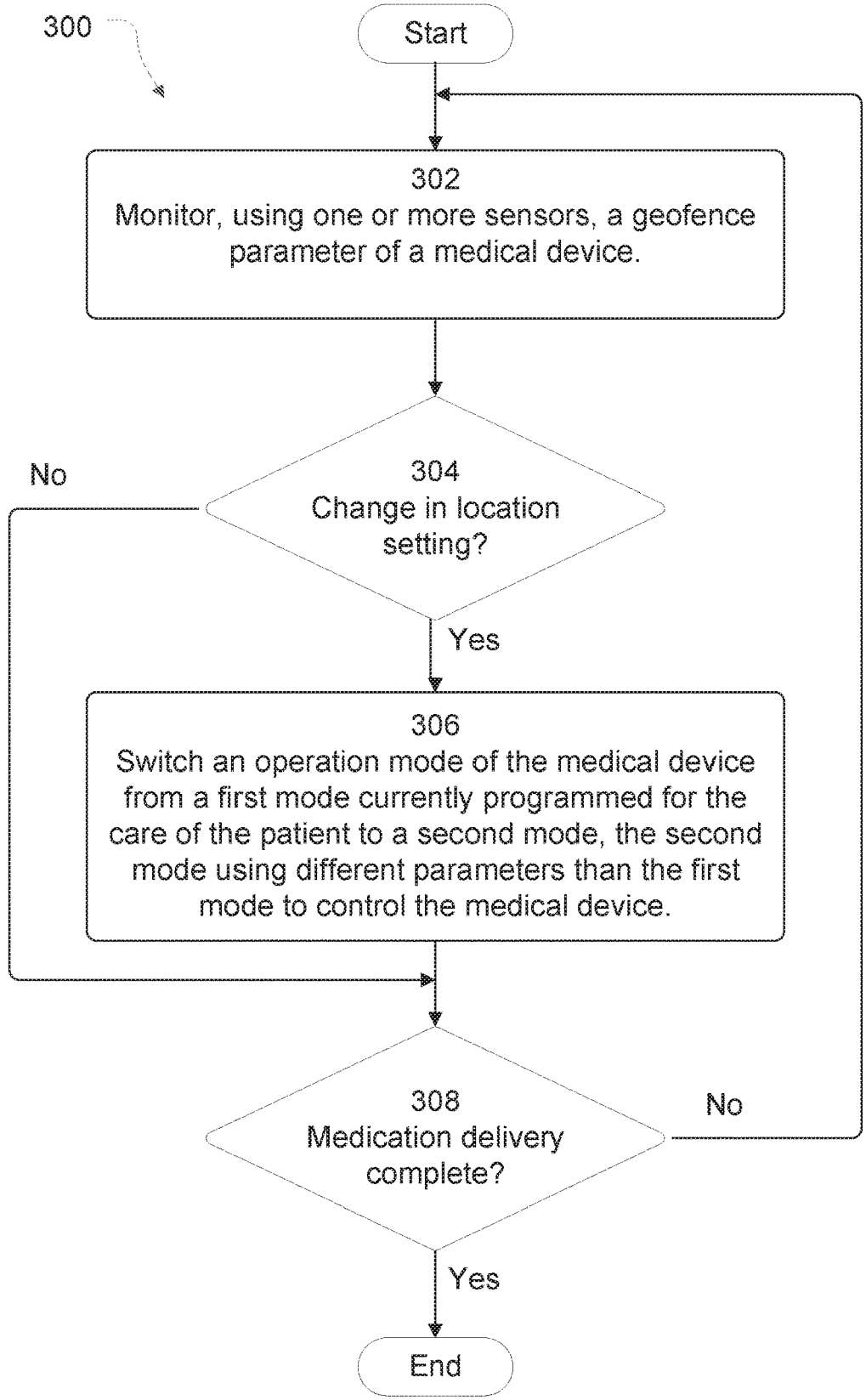
FIG. 3 depicts an example process for automatically adapting control of a medical device responsive to detecting a change in a location setting, according to aspects of the subject technology.

FIG. 3 depicts an example process for automatically adapting control of a medical device responsive to detecting a location change, according to aspects of the subject technology. For explanatory purposes, the various blocks of example process 300 are described herein with reference to FIGS. 1 and 2, and the components and/or processes described herein. The one or more of the blocks of process 300 may be implemented, for example, by one or more computing devices including, for example, medical device 12. In some implementations, one or more of the blocks may be implemented apart from other blocks, and by one or more different processors or devices. Further for explanatory purposes, the blocks of example process 300 are described as occurring in serial, or linearly. However, multiple blocks of example process 300 may occur in parallel. In addition, the blocks of example process 300 need not be performed in the order shown and/or one or more of the blocks of example process 300 need not be performed.

In the depicted example, a medical device monitors, using one or more sensors, a geofence parameter of a medical device in step 302. For example, the geofence parameter may be a GPS signal, a wireless network information (e.g., network name, access point identifier, cell identifier, etc.) or signal (e.g., LTE, Bluetooth), a wired network information (e.g., network name, access point identifier, etc.) or signal (e.g., TCP/IP message), location identifier (e.g., geospatial coordinate(s), place ID, etc.), or the like.

In step 304, a location setting change is determined based on the geofence parameter. For example, the location setting may be changed from one to another of a clinical care facility, a non-clinical setting such as a patient's home or a medical transport vehicle such as an ambulance or a medical helicopter.

Responsive to the determined location mode, an operation mode of the medical device is automatically switched from a first mode currently programmed for the care of the patient to a second mode, the second mode using different parameters than the first mode to control the medical device, in step 306. For example, a clinician mode may be geared towards use in a care facility with specific resources available to the device (e.g., network bandwidth, power, network security) and trained clinicians to operate the medical device, while a patient mode may be geared towards use in a patient's home with different resources and/or by the patient or a family member. In some implementations, the switching of operation mode may include identifying the operation mode to switch based on the geofence parameter. For example, if a geofence parameter may be associated with a specific care setting where certain modes are appropriate. The association may be stored as a static or dynamic configuration of the medical device within a memory accessible by the medical device.

According to various implementations, the previously described monitoring in step 302 may be continued or repeated (e.g., periodically) while a medication is being delivered. In the depicted example of FIG. 3, the medical device (and/or server 30 on behalf of the medical device) periodically determines (e.g., after each measurement) whether an ongoing medication delivery has completed in step 308. If not completed ("No"), the monitoring continues (e.g., return to step 302). If the medication delivery has completed ("Yes"), then the monitoring ends.

In some implementations, switching the operation mode of a medical device may include entering a power savings mode. The medical device may determine a battery capacity of a battery powering at least the hardware component of the medical device and determine that the battery capacity is insufficient to power the hardware component for a predetermined period of time. In this regard, switching the operation mode may include adjusting operation parameters used to control at least the hardware component to a reduce a power load of the medical device, and the power load may be reduced to a level sufficient for the battery to power the hardware component for the predetermined period of time.

As described previously, the medical device 12 may include a control unit 14, 204 configured to interface with multiple functional modules 16, 18, 20, 22 and to control and provide power to a respective functional unit when the functional unit is connected to the control unit. In some implementations, the medical device 12 may determine a battery capacity of a battery powering the control unit and a plurality of functional units currently connected to the control unit. This determination may be responsive to location setting change or may be performed periodically by a battery management system (e.g., circuit and/or software). The medical device may, based on the location of the medical device, determine that the battery capacity is insufficient to power the plurality of functional units for a predetermined period of time, and disable at least one of the plurality of functional units responsive to determining that the battery capacity is insufficient. In some implementations, the medical device may determine that the battery capacity is insufficient to power more than the at least one functional unit currently connected to the control unit for a predetermined period of time, and disable the control unit's ability to provide power to any additional functional units other than the at least one functional unit currently connected to the control unit responsive to determining that the battery capacity is insufficient.

Many steps of the above-described example process 300, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 4:
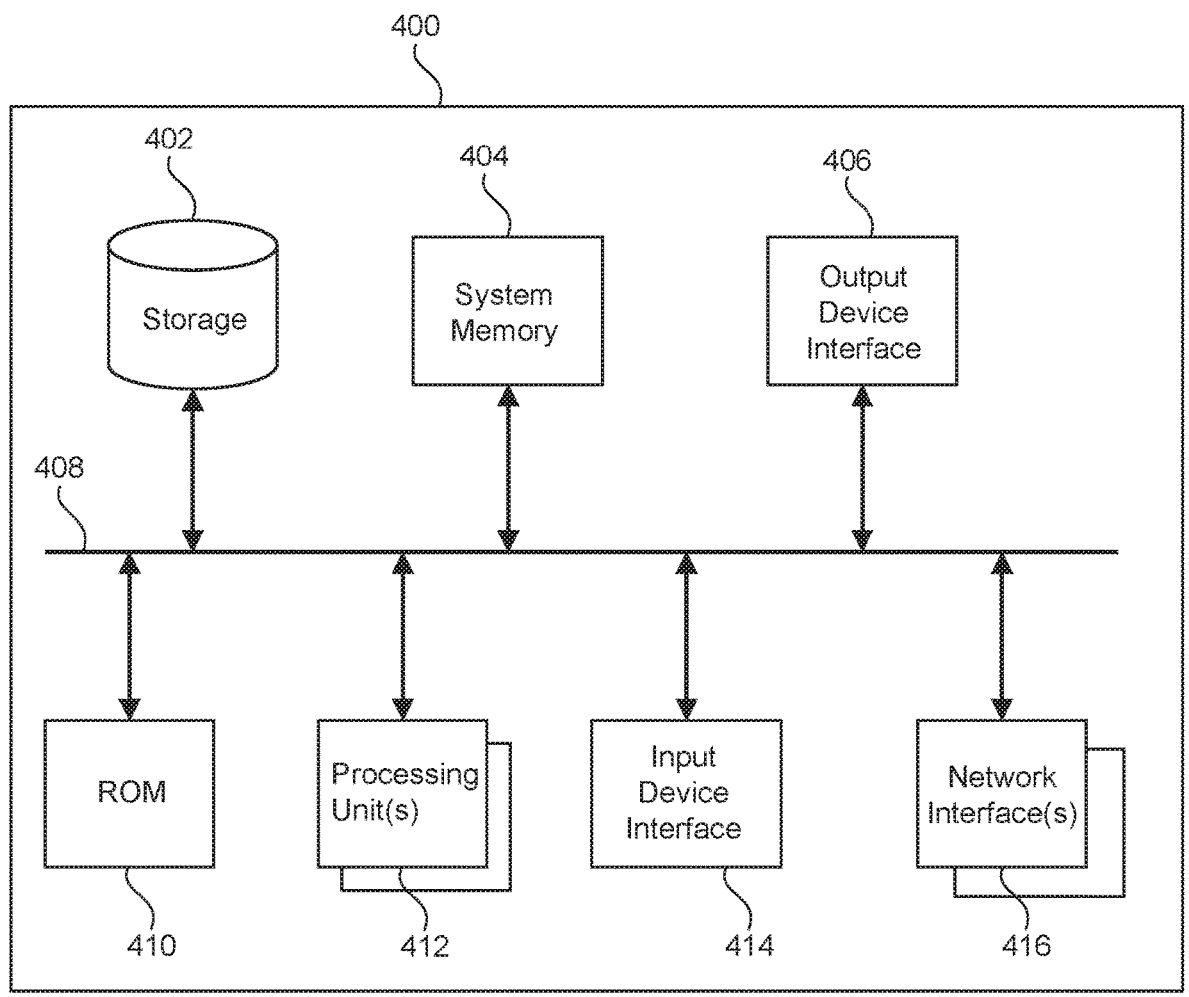
FIG. 4 is a conceptual diagram illustrating an example electronic system for adapting control of a medical device responsive to detecting a change in a geofence environment, according to aspects of the subject technology.

FIG. 4 is a conceptual diagram illustrating an example electronic system 400 for automatically adapting control of a medical device responsive to detecting a location setting change, according to aspects of the subject technology. Electronic system 400 may be a computing device for execution of software associated with one or more portions or steps of process 300, or components and processes provided by FIGS. 1-3, including but not limited to information system server 30, device terminal 32, computing hardware within patient care device 12, or external database 37. Electronic system 400 may be representative, in combination with the disclosure regarding FIGS. 1-3. In this regard, electronic system 400 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 400 may include various types of computer readable media and interfaces for various other types of computer readable media. In the depicted example, electronic system 400 includes a bus 408, processing unit(s) 412, a system memory 404, a read-only memory (ROM) 410, a permanent storage device 402, an input device interface 614, an output device interface 406, and one or more network interfaces 416. In some implementations, electronic system 400 may include or be integrated with other computing devices or circuitry for operation of the various components and processes previously described.

Bus 408 collectively represents all system, peripheral, and chipset buses that communicatively connect the numerous internal devices of electronic system 400. For instance, bus 408 communicatively connects processing unit(s) 412 with ROM 410, system memory 404, and permanent storage device 402.

From these various memory units, processing unit(s) 412 retrieves instructions to execute and data to process in order to execute the processes of the subject disclosure. The processing unit(s) can be a single processor or a multi-core processor in different implementations.

ROM 410 stores static data and instructions that are needed by processing unit(s) 412 and other modules of the electronic system. Permanent storage device 402, on the other hand, is a read-and-write memory device. This device is a non-volatile memory unit that stores instructions and data even when electronic system 400 is off. Some implementations of the subject disclosure use a mass-storage device (such as a magnetic or optical disk and its corresponding disk drive) as permanent storage device 402.

Other implementations use a removable storage device (such as a floppy disk, flash drive, and its corresponding disk drive) as permanent storage device 402. Like permanent storage device 402, system memory 404 is a read-and-write memory device. However, unlike storage device 402, system memory 404 is a volatile read-and-write memory, such a random access memory. System memory 404 stores some of the instructions and data that the processor needs at runtime. In some implementations, the processes of the subject disclosure are stored in system memory 404, permanent storage device 402, and/or ROM 410. From these various memory units, processing unit(s) 412 retrieves instructions to execute and data to process in order to execute the processes of some implementations.

Bus 408 also connects to input and output device interfaces 414 and 406. Input device interface 414 enables the user to communicate information and select commands to the electronic system. Input devices used with input device interface 414 include, e.g., alphanumeric keyboards and pointing devices (also called "cursor control devices"). Output device interfaces 406 enables, e.g., the display of images generated by the electronic system 400. Output devices used with output device interface 406 include, e.g., printers and display devices, such as cathode ray tubes (CRT) or liquid crystal displays (LCD). Some implementations include devices such as a touchscreen that functions as both input and output devices.

Also, as shown in FIG. 4, bus 408 also couples electronic system 400 to a network (not shown) through network interfaces 416. Network interfaces 416 may include, e.g., a wireless access point (e.g., Bluetooth or WiFi) or radio circuitry for connecting to a wireless access point. Network interfaces 416 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 400 can be used in conjunction with the subject disclosure.

Figure 5:
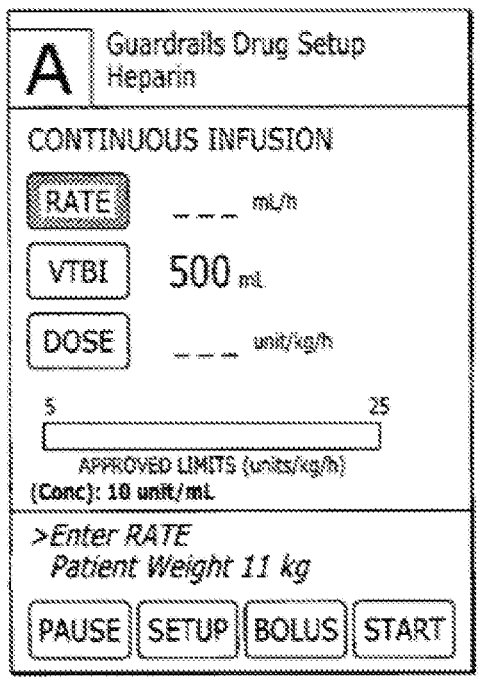
FIG. 5 is an illustration of an example graphical user interface that may be presented in a clinical geofenced area.

FIG. 5 is an illustration of an example graphical user interface that may be presented in a clinical geofenced area. The clinician GUI includes technical details and several control elements (e.g., buttons) to adjust a state of the medical device. The clinician GUI may be presented when the medical device is within a location identified as being a clinical area such as within a hospital or other health care facility.

Figure 6:
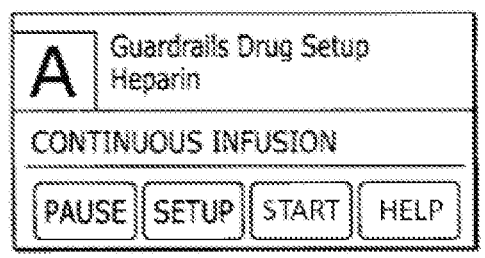
FIG. 6 is an illustration of an example graphical user interface that may be presented in a non-clinical geofenced area.

FIG. 6 is an illustration of an example graphical user interface that may be presented in a non-clinical geofenced area. The non-clinical GUI includes fewer details than the clinical GUI shown in FIG. 5. Some functionality of the clinical GUI are removed (e.g., bolus button) and some functionality is added (e.g., help button). The non-clinical GUI may be presented when the medical device is within a location identified as non-clinical such as at a patient's home.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

The dynamic user interface may also provide security during medication administration. In some implementations, the quantity of a medication to be administered should be carefully controlled to prevent overdosing and subsequent harm to the patient. By restricting access to interface elements that can be changed based on location, the administration parameters may be secured from inadvertent or intentional adjustment outside controlled environments. For example, a patient with dementia may not be capable of safely adjusting a parameter of an infusion pump. Accordingly, the parameters may be hidden when the pump is detected within the patient's home. However, when the patient is transported to a care giver's home (e.g., a child), after the pump detects the new location as being within a permissible geofenced location, the parameter adjustment interface may be enabled.

The adjustments may include adjusting a hardware function of the pump. For example, the door of the pump may be secured until the pump returns to an appropriate location. As another example, physical buttons on the pump may be disabled until the pump returns to a designated location. As another example, the pump may include a wireless transceiver, a pump motor, or a battery. The power provided by the battery to one or more of the wireless transceiver or the pump motor are additional hardware functions that may be adjusted based on the features described.

The functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra-density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

Various devices described may "provide" messages, alerts, alarms, power, interfaces or other operational outputs. The use of these terms (e.g., "provide" or "providing") in this manner encompasses a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. An infusion pump, comprising:
   a housing;
   a wireless transceiver;
   a pump motor mounted within the housing, wherein a force from the pump motor causes delivery of a fluid from a fluid source to a patient;
   a location sensor configured to provide information associated with a location of the infusion pump;
   a battery conductively coupled with: (a) the wireless transceiver to provide power to communicate messages via the wireless transceiver; (b) the pump motor to provide power to activate the pump motor, and (c) the location sensor to provide power to activate the location sensor;
   one or more processors conductively coupled with the battery; and
   memory including instructions that, when executed by the one or more processors, cause the infusion pump to:
   monitor, using the location sensor, a geofence parameter of the infusion pump, the geofence parameter comprising one of a location and environment of the medical device;
   determine a change in the location of the infusion pump based on the geofence parameter;
   identify an operation mode of the infusion pump associated with the geofence parameter;
   automatically switch, responsive to the changed location, the operation mode of the infusion pump from a first mode currently programmed for care of the patient to a second mode for care of the patient, the second mode using a second geofence parameter different than a first geofence parameter used by the first mode to control at least one of the battery, the pump motor, or the wireless transceiver of the infusion pump;
   determine one of a quantity of medication available to be dispensed by the infusion pump and a battery capacity of the battery;
   determine, based on the change in location of the infusion pump, one of the quantity of medication is insufficient to follow a current medication dispensing protocol of the infusion pump and the battery capacity is insufficient to power the infusion pump for a predetermined period of time; and
   generate an alert according to an alerting sequence associated with the second mode, wherein one of the second mode is associated with a clinical care facility and the alerting sequence is adjusted to behave according to alerting escalation rules used by the clinical care facility, and the second mode is associated with a home care location and the alerting sequence is adjusted to behave according to predetermined home alerting escalation rules.

2. A method, comprising:
   monitoring, using one or more sensors, a geofence parameter of a medical device, the geofence parameter comprising one of a location and environment of the medical device;
   determining a change in a location setting of the medical device based on the geofence parameter;
   automatically switching, responsive to the changed location setting, an operation mode of the medical device from a first mode currently programmed for care of a patient to a second mode for care of the patient, the second mode using second parameters to control the medical device, the second parameters being different than first parameters used by the first mode to control the medical device;
   determining a quantity of medication available to be dispensed by the medical device;
   determining, based on the location setting exceeding a distance range over which the determined quantity of medication is to be dispensed, that the quantity of medication is insufficient to follow a current medication dispensing protocol of the medical device; and
   generating an alert according to an alerting sequence associated with the second mode.

3. The method of claim 2, wherein switching the operation mode of the medical device comprises switching from a clinician based functional module to a non-clinician based functional module.

4. The method of claim 2, wherein switching the operation mode of the medical device comprises switching from a non-clinician based functional module to a clinician based functional module.

5. The method of claim 2, wherein the medical device comprises an infusion device and the one or more sensors comprises one of a global positioning system receiver, a radio frequency receiver, a Bluetooth receiver and a cellular receiver, and the operation mode is associated with a pumping mechanism administering a fluid to the patient.

6. The method of claim 2, further comprising:
   determining a battery capacity of a battery powering the medical device;
   determining, based on the location setting exceeding a distance range over which the battery needs to power the medical device, that the battery capacity is insufficient to power the medical device for a predetermined period of time; and
   generating an alert according to an alerting sequence associated with the second mode.

7. The method of claim 6, wherein the second mode is associated with a clinical care facility and the alerting sequence is adjusted to behave according to alerting escalation rules used by the clinical care facility.

8. The method of claim 6, wherein the second mode is associated with a home care location and the alerting sequence is adjusted to behave according to predetermined home alerting escalation rules.

9. The method of claim 2, wherein switching the operation mode of the medical device comprises switching information provided on a user interface device from information associated with the first mode to information associated with the second mode.

10. The method of claim 9, wherein the information associated with the second mode that is provided on the user interface device is one of a clinician interface configured for use by a trained clinician and a simplified format interface configured for use by a non-clinical user.

11. A medical device, comprising:
one or more processors; and
memory including instructions that, when executed by the one or more processors, cause the medical device to:
monitor, using one or more sensors, a geofence parameter of the medical device;
determine a change in a location setting of the medical device based on the geofence parameter;
automatically switching, responsive to the changed location setting, an operation mode of the medical device from a first mode currently programmed for care of a patient to a second mode, the second mode using different parameters than the first mode to control the medical device;
determine a battery capacity of a battery powering the medical device;
determine, based on the location setting exceeding a distance range over which the battery needs to power the medical device, that the battery capacity is insufficient to power the medical device for a predetermined period of time; and
generate an alert according to an alerting sequence associated with the second mode,
wherein one of the second mode is associated with a clinical care facility and the alerting sequence is adjusted to behave according to alerting escalation rules used by the clinical care facility, and the second mode is associated with a home care location and the alerting sequence is adjusted to behave according to predetermined home alerting escalation rules.

12. The medical device of claim 11, wherein switching the operation mode of the medical device comprises one of switching from a clinician based functional module to a non-clinician based functional module and switching from a non-clinician based functional module to a clinician based functional module.

13. The medical device of claim 11, wherein the medical device comprises an infusion device and the one or more sensors comprises one of a global positioning system receiver, a radio frequency receiver, a Bluetooth receiver and a cellular receiver, and the operation mode is associated with a pumping mechanism administering a fluid to the patient.

14. The medical device of claim 11, wherein the instructions, when executed by the one or more processors, further cause the medical device to:
determine a quantity of medication available to be dispensed by the medical device;
determine, based on the location setting exceeding a distance range over which the determined quantity of medication is to be dispensed, that the quantity of medication is insufficient to follow a current medication dispensing protocol of the medical device; and
generate an alert according to an alerting sequence associated with the second mode.

15. The medical device of claim 11, wherein switching the operation mode of the medical device comprises switching a user interface module from information associated with the first mode to information associated with the second mode.

16. The medical device of claim 15, wherein the user interface module is a clinician user interface configured for use by a clinician trained on using the clinician user interface.

17. The medical device of claim 15, wherein the user interface module is a simplified patient user interface configured for use by one of a patient and a non-trained user associated with the patient.

* * * * *